(12) United States Patent  
Sexton

(10) Patent No.: US 10,864,973 B2
(45) Date of Patent: Dec. 15, 2020

(54) SELF-INFLATING PERSONAL FLOATATION DEVICE ("SIPFD")

(71) Applicant: Jordan Denning Sexton, Houston, TX (US)

(72) Inventor: Jordan Denning Sexton, Houston, TX (US)

(*) Notice: Subject to any disclaimer, the term of this patent is extended or adjusted under 35 U.S.C. 154(b) by 0 days.

(21) Appl. No.: 16/778,598

(22) Filed: Jan. 31, 2020

(65) Prior Publication Data

US 2020/0164953 A1    May 28, 2020

Related U.S. Application Data

(63) Continuation of application No. 16/576,011, filed on Sep. 19, 2019, now Pat. No. 10,589,828.

(60) Provisional application No. 62/734,033, filed on Sep. 20, 2018.

(51) Int. Cl.
*B63C 9/20* (2006.01)
*B63C 9/125* (2006.01)
*G01F 23/00* (2006.01)
*A61B 5/0468* (2006.01)
*H04W 4/029* (2018.01)

(52) U.S. Cl.
CPC .............. *B63C 9/20* (2013.01); *A61B 5/0468* (2013.01); *B63C 9/1255* (2013.01); *G01F 23/00* (2013.01); *H04W 4/029* (2018.02)

(58) Field of Classification Search
CPC ........ B63C 9/1255; B63C 9/20; H04W 4/029; A61B 5/0468; G01F 23/00
See application file for complete search history.

(56) References Cited

U.S. PATENT DOCUMENTS

| | | | | |
|---|---|---|---|---|
| 6,659,825 | B2 * | 12/2003 | Foss | B63C 9/155 |
| | | | | 441/123 |
| 6,970,731 | B1 * | 11/2005 | Jayaraman | A61B 5/0008 |
| | | | | 600/388 |
| 9,737,261 | B2 * | 8/2017 | Coza | A61B 5/0022 |
| 9,756,883 | B1 * | 9/2017 | Luevano | B63C 9/115 |
| 10,159,440 | B2 * | 12/2018 | Longinotti-Buitoni | |
| | | | | A41D 1/002 |
| 10,165,946 | B2 * | 1/2019 | Bardy | A61B 5/7282 |
| 10,244,986 | B2 * | 4/2019 | Adams | A61B 5/6833 |
| 10,414,475 | B2 * | 9/2019 | Sunol | A61B 5/0488 |
| 10,462,898 | B2 * | 10/2019 | Longinotti-Buitoni | |
| | | | | A61B 5/7455 |
| 2008/0266118 | A1 * | 10/2008 | Pierson | A61B 5/6826 |
| | | | | 340/573.6 |

* cited by examiner

*Primary Examiner* — Stephen P Avila
(74) *Attorney, Agent, or Firm* — Nolte Lackenbach Siegel

(57) ABSTRACT

A self-inflating personal flotation device ("SIPFD") configured to be worn by a wearer and aid the wearer automatically. The SIPFD may communicate with a global communication network and pressurized gas cartridge assembly based on a triggering event. The SIPFD may have a wearable data transmitter of a heartbeat device; a water depth device; and a geolocation device. The SIPFD may have a neck inflation device and a torso inflation device both connected to the pressurized gas cartridge assembly to enable the pressurized gas cartridge to inflate the neck and torso inflation devices when prompted. The prompt may be automatic or on request and be performed using an actuator mechanically communicating with the pressurized gas cartridge assembly to: (i) inflate the neck and torso inflation devices; and (ii) deflate the neck and torso inflation devices associated with a wearer.

15 Claims, 7 Drawing Sheets

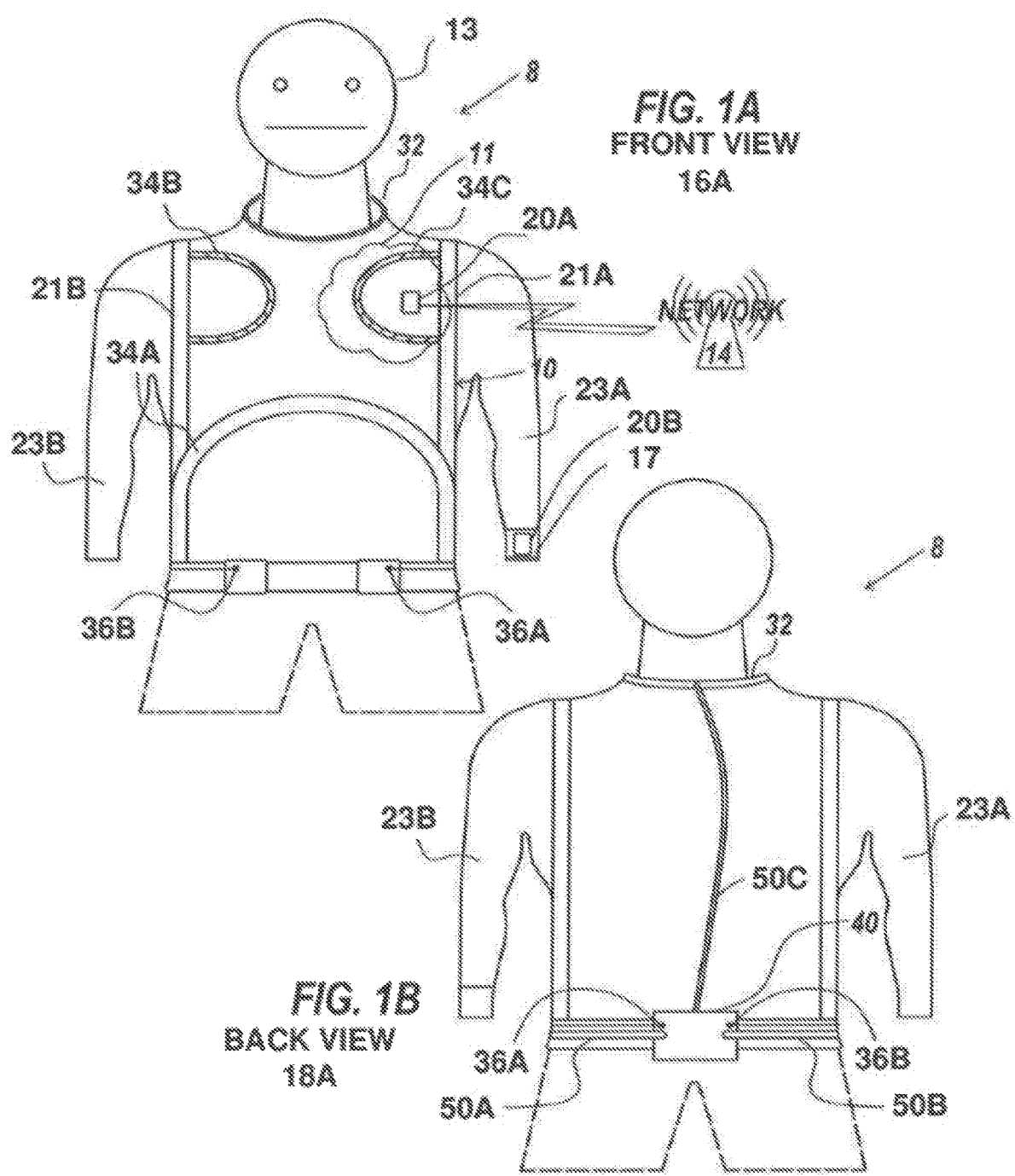

FRONT VIEW
16B

BACK VIEW 18B

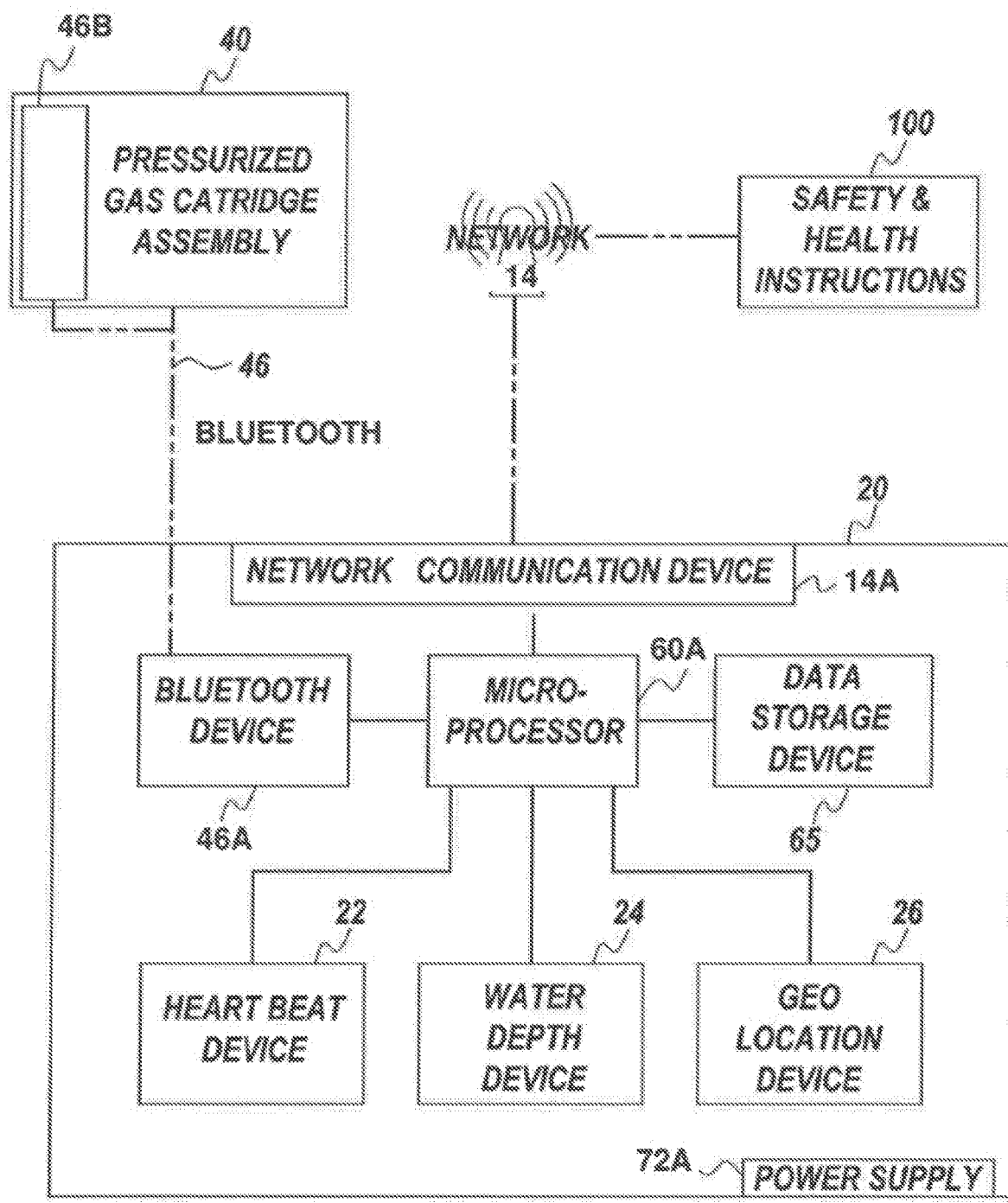

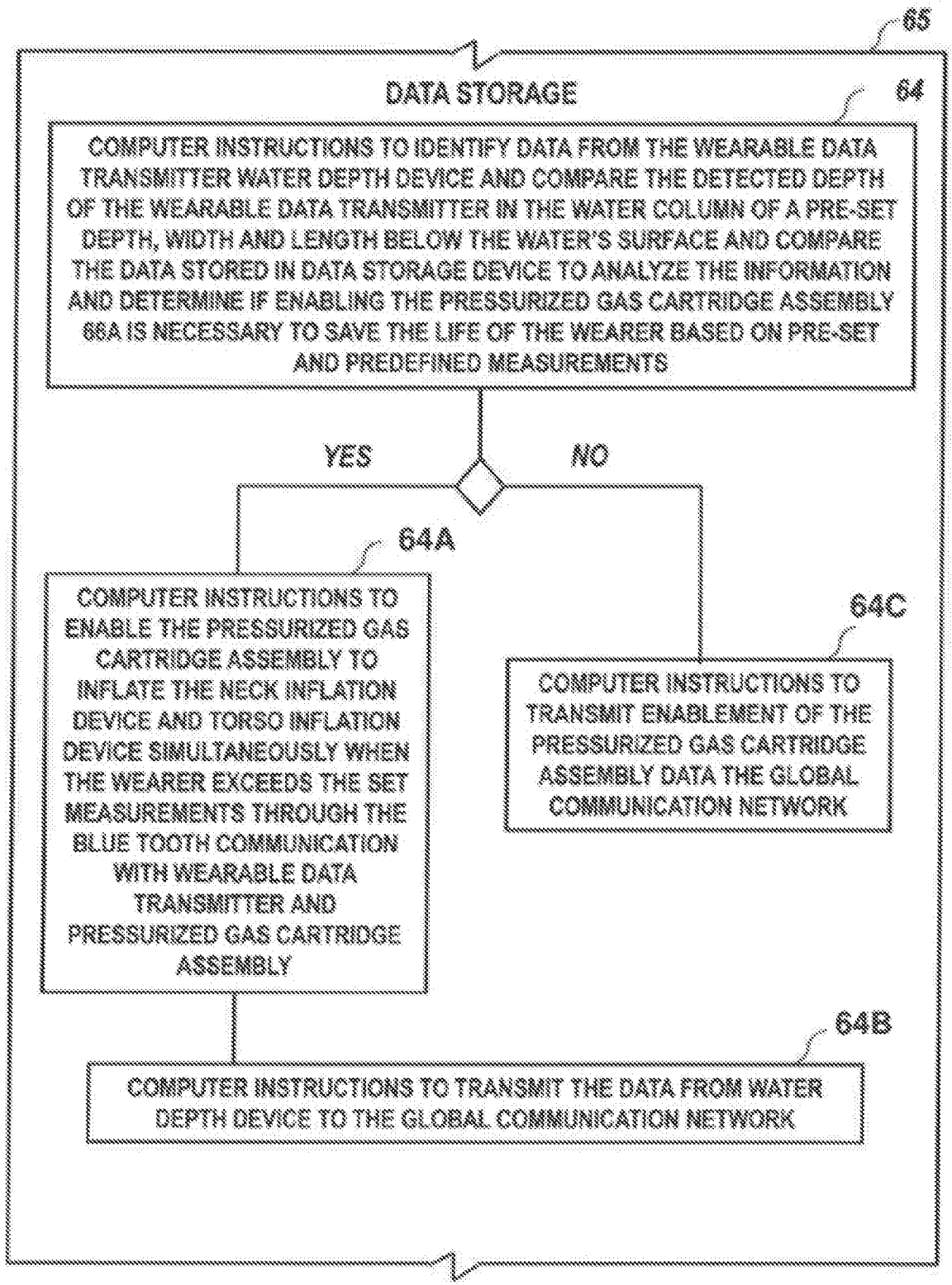

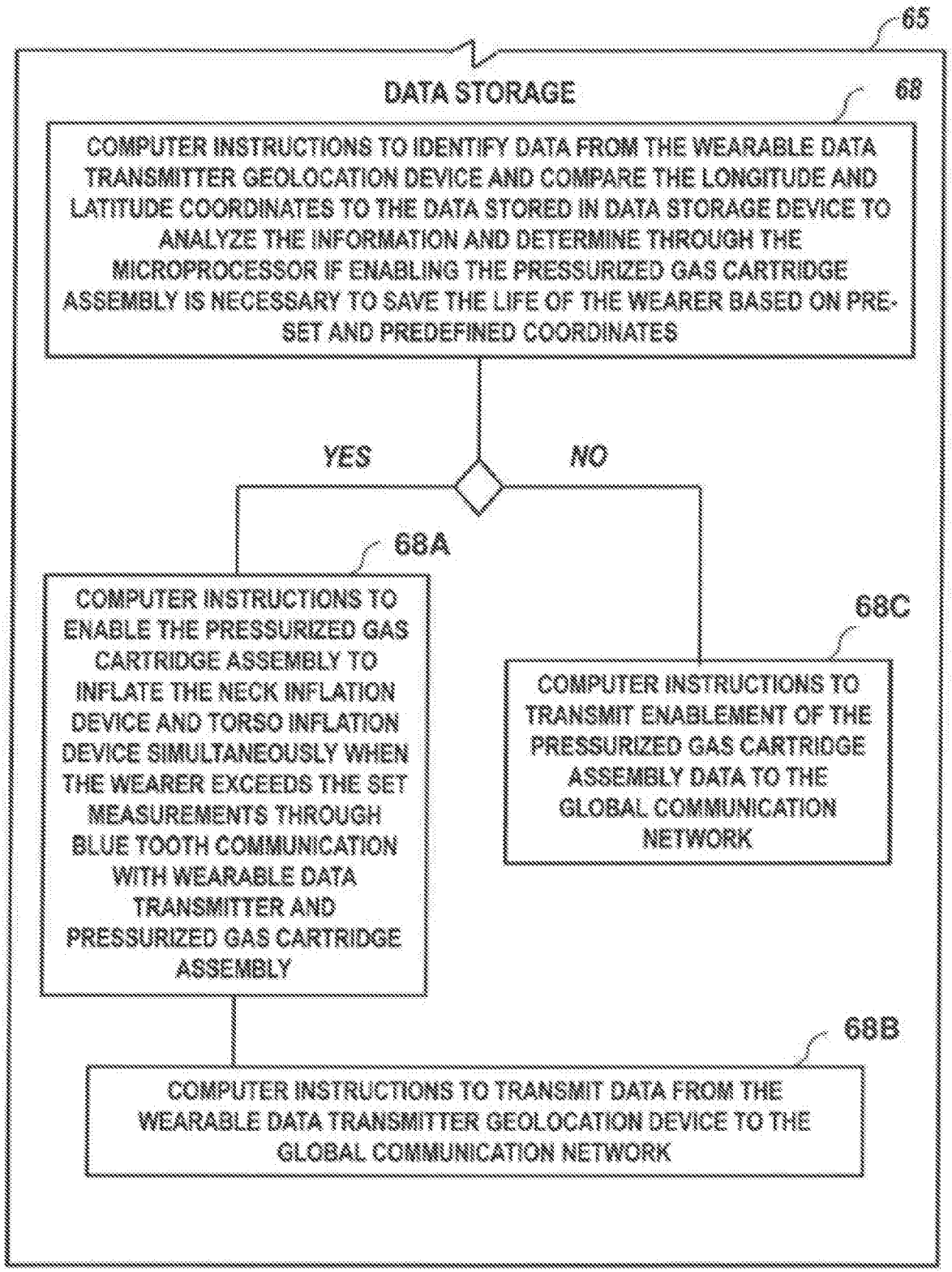

US 10,864,973 B2

SELF-INFLATING PERSONAL FLOATATION DEVICE ("SIPFD")

CROSS-REFERENCE TO RELATED CASES

This application is a Continuation application of co-pending U.S. non-provisional application Ser. No. 16/576,011 filed Sep. 19, 2019 which claims priority to U.S. Provisional Application No. 62/734,033 filed Sep. 20, 2018, each of which are entitled "Self-Inflating Personal Flotation Device," having the same inventorship, and both of which are incorporated by reference in their entirety for all applicable purposes to the extent consistent herewith.

FIELD

The present embodiment generally relates to a self-inflating personal flotation device ("SIPFD").

BACKGROUND

A need exists to gather data immediately and provide instantaneous inflation in the event of a heart attack, unconsciousness, or inability to stay afloat in a body of water after such an event. Physically demanding activities performed in large bodies of water, such as a lake or ocean, may increase the likelihood of such an event. In some cases, sudden physical impairment may occur, for example, during a triathlon or swim training.

An additional need exists to gather data immediately and provide instantaneous inflation in the event of an emergency while working on an oil and gas rig at sea or located off-shore (e.g., in an ocean).

A still further need exists to gather data immediately and provide instantaneous inflation in the event of an emergency while working on a commercial fishing vessel at sea or ocean.

This disclosure introduces a device including components to collectively provide an SIPFD to address these and other needs. In some instances, the disclosed SIPFD may provide potentially lifesaving assistance to persons in distress.

BRIEF DESCRIPTION OF THE DRAWINGS

The detailed description will be better understood in conjunction with the accompanied drawings as follows:

FIGS. 1A-1B depict the front and back of a shirt enhanced to incorporate an SIPFD according to one or more disclosed embodiments;

FIG. 2 depicts the wearable data transmitter to provide data (health, location, state metrics, etc.) regarding a person in potential distress that may be used in conjunction with a SIPFD according to one or more embodiments;

FIGS. 4A-C depict example data flows for a processor communicatively coupled to a wearable data transmitter and a pressurized gas cartridge assembly to provide internal device communication and external data transmission to implement an SIPFD according one or more embodiments.

Figure 1C:
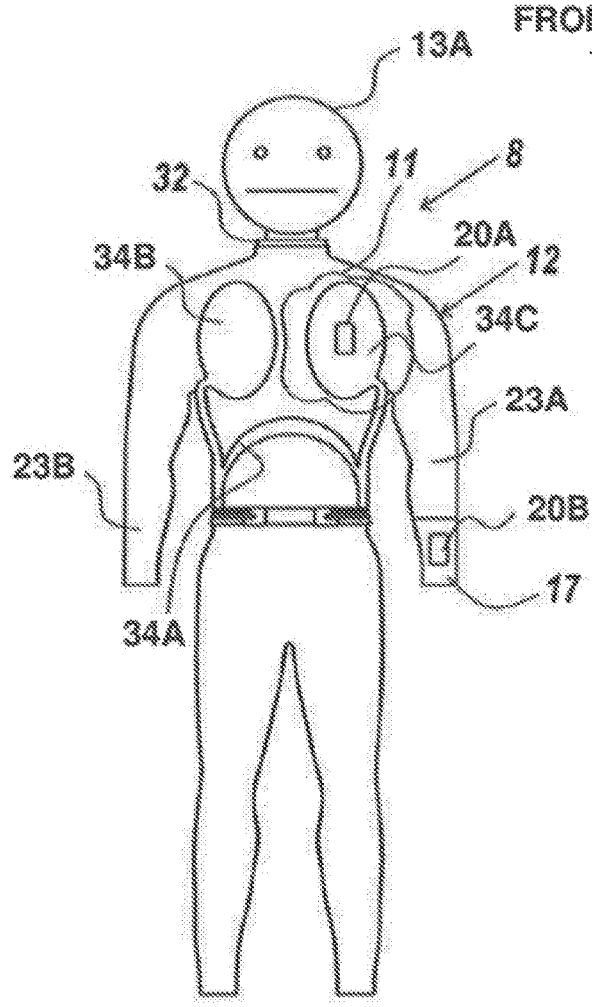
FIGS. 1C-1D depict a wetsuit enhanced to incorporate a SIPFD according to one or more embodiments.

Example embodiments are detailed below with reference to the listed Figures. Different embodiments are also possible and will be recognizable to one of ordinary skill in the art, given the benefit of this disclosure, without departing from the scope presented herein. As is common in the practice, drawings are not necessarily drawn to scale and are for explanatory purposes that are not meant to limit elements beyond the language of the claims. Except for reasons of clarity, like elements from the different figures are presented with the same or similar element numbers, although not all repeated elements are necessarily numbered in all FIGs.

DETAILED DESCRIPTION

Before explaining the disclosed different embodiments of an SIPFD apparatus in detail, it is to be understood that the apparatus is not limited to the particular embodiments and that it can be practiced or carried out in various ways.

This disclosure relates to a safety device to assist a person that is intending to be in water or unexpectedly presented with a need for flotation assistance (namely an SIPFD). The SIPFD apparatus, in its different embodiments, may include monitors to determine a state of a wearer (e.g., health and physical state) and to automatically perform actions based on that state determination. The SIPFD apparatus is intended to be non-intrusive to activities performed by the wearer such that it may be worn while the user is performing many different physical activities. For example, the device may be worn by personnel performing a work function on an oil-rig, shipping vessel, or other work activity where a potential water immersion is possible. Also, the device may be worn during recreational or sporting activities without impeding enjoyment or performance of the activity.

In general, the SPIFD apparatus is configured to be worn by a wearer (or user) and communicate with a global communication network to provide information that may include a geo-location of the wearer. The device may incorporate one or more pressurized gas cartridges as part of a gas cartridge assembly to assist in flotation of the wearer based on an automatic determination that assistance is required. Of course, the device may also include a manual activation capability.

To accomplish the goal of aiding, the device may include a wearable data transmitter encapsulating a heartbeat device; a water depth device; and a geolocation device. The floatation device may have a neck inflation device and/or a torso inflation device that may both be connected to a pressurized gas cartridge assembly through tubing. The device may include a mechanically activated emergency actuator that is mechanically configured to activate the pressurized gas cartridge assembly (e.g., via puncturing or opening a valve) to: (i) inflate the neck and torso inflation devices; and (ii) deflate the neck and torso inflation devices.

As referenced herein, the term "BLUETOOTH® device" refers to an open wireless technology standard for transmitting fixed and mobile electronic device data over short distances. Wireless technology may be used for simplified communication between the sensors, micro-processors, devices, networks, and servers. Although disclosed embodiments reference BLUETOOTH®, other wireless technologies may be used (e.g., near field communication ("NFC")) for different functions or to provide a set of non-interfering concurrent wireless communication capabilities between different components of the apparatus. Other examples of wireless communication may include, Translational Acoustic-RF communication ("TARF") that may be used to enable communication between underwater sources and the air. In one example, a TARF transmitter sends standard sound (or SONAR signals). Sound travels as pressure waves within the water. Accordingly, when these pressure waves hit the surface of the water, they cause the surface of the water to vibrate. Vibrations may then be sensed from the air that has been caused to vibrate. Specifically, a TARF receiver in the air may use a very sensitive radar to detect the vibrations. The radar of the TARF receiver may, for example, transmit a signal which reflects off the water surface and reflects back (e.g., causing a "reflected signal"). As the water surface vibrates, it causes small changes to be imparted into the reflected signal that may be detected in the received radar signal at the TARF receiver. Overall, this combination of functions may enable a TARF receiver to sense the tiny vibrations caused by the underwater acoustic transmitter that caused the original pressure waves in the water. Analysis of this combination of signals thus enable communication between underwater sources (e.g., underwater acoustic transmitter) and a receiver in the air outside the water.

The term "data storage device" refers any computing hardware that is used for storing, porting, and extracting data files and objects. It can hold and store information both temporarily and permanently, and can be internal or external to a computer, server, or any similar computing device.

The term "ECG" refers to an electrocardiogram ("ECG") device that may be a sensor or incorporated into another sensor performing multiple functions. An ECG is generally, a personal monitoring device that detects, determines, and provides the timing and strength of the electrical impulses generated by a person's heartbeat. For example, an ECG may monitor signals from special cells in the upper right chamber of a person's heart (pacemaker cells) and track these signals as they travel through a person's heart back to the electrocardiogram device. In some cases, a sensor using an ECG may monitor in real time and/or record the heart measurements for later study.

The term "geolocation device" refers to a device that detects, determines, and provides the exact location of a computer, networking device, or equipment that incorporates the geolocation device. The location is typically based on geographical longitude and latitude coordinates and measurements. Geolocation provides the location of a device but is generally used in a variety of applications to help locate human users. Geolocation typically works through a GPS ("Global Positioning System") in a device that propagates the device's longitudinal and latitudinal coordinates. The coordinates may then be identified on a map to provide an accurate location for the device. The map may be cross-referenced using a specific longitude and latitude point to provide a mapped location of the device in a body of water, country, city, town/colony, building name and street address. In addition to GPS, geolocation also may be identified or validated through an Internet Protocol ("IP") address; a media access control ("MAC") address; using radio frequency ("RF") systems; using Exchangeable Image File Format ("EXIF") data; and other wireless positioning systems. In some case, triangulation of different signals or data points may be used to further refine or obtain a geolocation.

The term "heartbeat device" refers to a sensor that detects, determines and provides heart rate measurements and heart ECG (aka: EKG) measurements of a wearer. A heartbeat device may function in conjunction with a computer, network device, or equipment that enables the device. Functionality of the heartbeat device may be based on predetermined, pre-set, or cognitively learned (e.g., through Artificial Intelligence ("AI")) measurements. A heartbeat device, in accordance with this disclosure, may also transmit the ECG information or raw data to a global communication network or data storage. A heartbeat device may be considered, in some instances, as a personal monitoring device that allows one to measure one's heart rate in real time or record the heart rate data for later study.

The term "neck inflation device" refers to an inflatable flotation device including one or more inflatable compartments (e.g., bladders) that are generally positioned around the collar of a wearer and may be configured to simultaneously inflate/deflate with the torso inflation device.

The term "network device" refers to physical devices which are used for communication and interaction between devices on a computer network. Specifically, they mediate data in a computer network. A network device may include a device connecting computers, sensors, or microprocessors to allow communication between the different devices. A network device may also be used to facilitate communication between a device and external devices that may be connected via networks, such as GPS and global communication networks. Networks may be computer networks, cellular networks, wireless networks, or the like.

The term "pressurized gas cartridge" refers a vessel use to store gases at above atmospheric pressure. For example, a pressurized gas cartridge may contain compressed gasses at different compression pressures, for example, from 5 psi to 150 psi. The pressurized gasses may be air, oxygen, carbon dioxide, nitrogen, or a combination there of. In some embodiments, the pressurized gas cartridge may be a small 16-35-gram gas cartridge, for example, the small size will not impede activities of a user.

The term "shirt" refers to a garment for the upper body or swim skin as may be used in triathlons or other endurance swimming events.

The term "torso inflation device" refers to an inflatable flotation device including one or more inflatable compartments (e.g., bladders) that are generally positioned on the front torso of a wearer and may also extend across the front torso from side to side. In some cases, a torso inflation device may include a pair of inflatable bladders positioned over the pectoral muscles of a wearer. The torso inflation device may be configured to simultaneously inflate/deflate with the neck inflation device.

The term "wearer" refers to a human, an air breathing pet, or another air breathing land based life form.

The term "water column" refers to a perimeter around a specific location or physical area. The perimeter would be the measurements of that specific locations water level in correlation with the width, length, and depth of the column below the surface of the water.

The term "water depth device" refers to a barometer and altimeter sensor that detects, determines and provides the measurements of the pressure and atmospheric altitude of a computer, network device, or equipment above or below a fixed level or water's surface to indicate the location of the equipment and an associated wearer. In some cases, a water depth device may be automatically enabled (e.g., activated) based on predetermined or pre-set measurements. In other words, the water depth device may be pre-programmed to trigger and cause an action in response to a determination that pressure and/or atmospheric altitude has reached a defined level.

The term "wetsuit" refers to a garment such as a close-fitting suit made of material (such as sponge rubber), neoprene, or similar wetsuit 3 mm gauge suit with a liner that is worn (as by a skin diver) especially in cold water to retain body heat and that traps a thin layer of water against the body to allow warming of the thin layer to assist in maintaining body temperature of the wearer.

The term "safety garment" refers to either of the above referenced wetsuit or shirt and is used to collectively refer to either implementation.

One benefit of the devices of this disclosure is the increased likelihood of saving lives, in part, by instantly detecting, determining, providing remotely, and automatically reacting to data obtained from an associated wearer. The wearer may be a person or another mammal. The disclosed devices may alone or in combination automatically inflate the neck inflation and/or torso inflation devices based on pre-set, predetermined, or cognitively learned (e.g., using AI) data to save the life of the wearer and prevent drowning in the instance the wearing cannot save one's self.

Another benefit of the disclosed device(s) is that the devices, either alone or in combination, may provide numerous remote entities (e.g., first responders and other safety and health institutions) at least a portion of the monitored data before, during, and after the detected triggering event (e.g., a potential traumatic event experienced by the wearer). In some cases, the disclosed devices may provide up to date heartbeat, water depth, and geolocation information. This data may be provided to the safety and health institutions to assist them in preventing injuries and casualties (or at least reduce the impact of such events). Specifically, after a triggering event, data may be provided remotely to assist in location of a wearer so that assistance may be directed to the appropriate location (e.g., transmitted geolocation).

Turning now to the FIGs., FIG. 1A and FIG. 1B respectively depict a front view 16A and a back view 18A of a shirt 10 enhanced to incorporate disclosed devices to function as described above (and in more detail below). The following description is directed to FIGS. 1A and 1B viewed together and reference numbers mentioned in the discussion may only appear in one of these two FIGs.

The SIPFD 8 can be a shirt 10 configured to be worn by a person or other living creature that communicates automatically with a global communication network 14 such as a satellite communication network, the Internet, or a similar network and a GPS network (not shown) simultaneously.

Shirt 10 is shown from a front view 16B in FIG. 1A and a back view 18A in FIG. 1B with two openings 21A and 21B. The openings 21A-B each allow one of a pair of appendages 23A-B of wearer 13 to extend through a respective opening.

A first wearable data transmitter 20A is securely attached to front torso area 11 of shirt 10 and/or a second wearable data transmitter 20B is positioned in wrist area 17A of wearer 13. Wearable data transmitter 20A-B communicates with a global communication network 14 and may be used to control functions of pressurized gas cartridge assembly 40.

In use, each wearable data transmitter 20 is configured to touch the wearer 13 to gather the sensor data from wearer 13 as well as transmit data to a global communication network 14 and to the pressurized gas cartridge assembly 40 simultaneously.

A neck inflation device 32 is positioned about the neck of a wearer 13 wherein the neck inflation bladder is configured to receive pressurized gas from the pressurized gas cartridge assembly 40 and is secured to the shirt 10.

A torso inflation device including multiple bladders is shown. Specifically, in this example, the torso inflation device has a lower U shape bladder 34A extending from side to side of shirt 10 over the front abdominal region of the wearer 13. The torso inflation device of this example additionally has a pair of upper C-shaped bladders including a right pectoral bladder 34B and a left pectoral bladder 34C.

As the name implies, each of these second and third bladders may be positioned over the pectoral muscles of the wearer 13 between the shirt 10 and the skin of the wearer 13. The neck and torso inflation devices are, in this example, both configured to receive pressurized gas simultaneously.

A set of mechanically activated emergency actuators 36A-B are, in some embodiments, mechanically connected with pressurized gas cartridge assembly 40 to: (i) inflate the neck and torso inflation devices; and (ii) deflate the neck and torso inflation devices by a wearer 13 or first responder.

In one embodiment, the back of shirt 10 (see back view 18A) includes the two openings 21A and 21B mentioned above to accommodate appendages of wearer 13. Pressurized gas cartridge assembly 40 may be attached to the back of shirt 10 on the outside of shirt 10 such that gas cartridge assembly 40 is positioned away from the skin of wearer 13. Further gas cartridge assembly 40 may be positioned in the region of the body commonly referred to as the "small of the back" or in another region so as to not impede movement of wearer 13.

In this example, a first tube 50C (see back view 18A), that may be located inside the back of shirt 10 (e.g., to prevent potential entanglement while in use), connects pressurized gas cartridge assembly 40 to neck inflation device 32.

In one embodiment, a second tubing 50A and a third tubing 50B, that may also be inside the back of shirt 10 (see back view 18A), connects pressurized gas cartridge assembly 40 to torso inflation devices 34B and 34C (positioned near pectoral region as shown in front view 16A).

Figure 3:
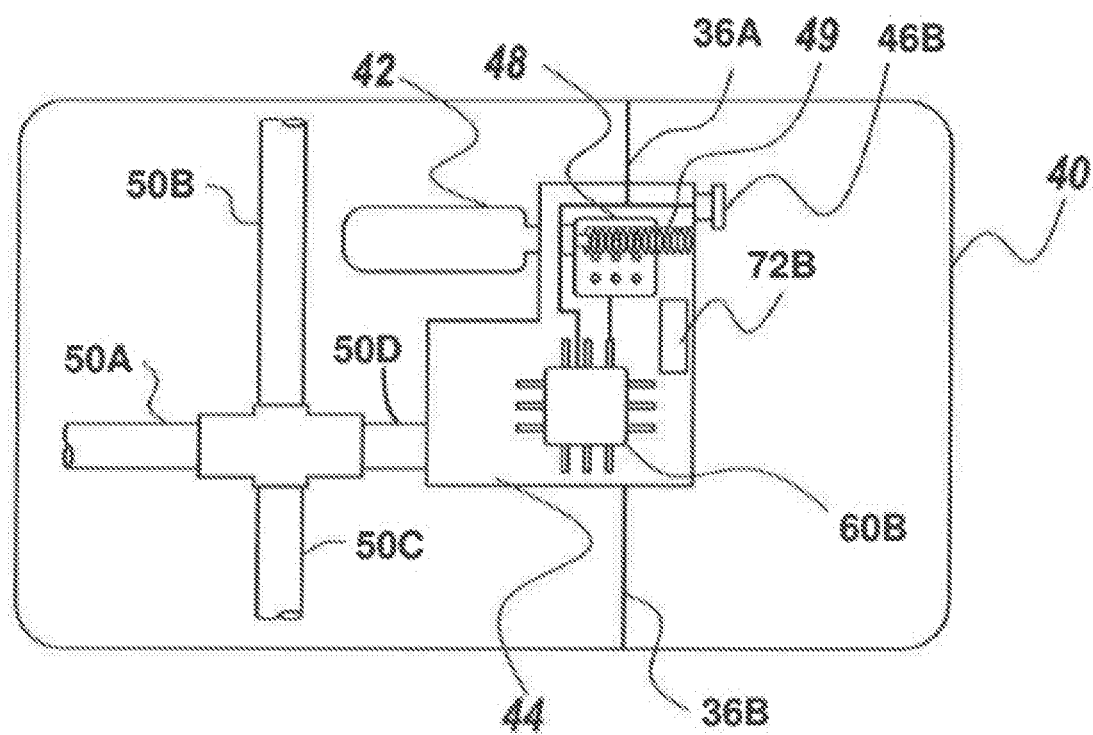
FIG. 3 depicts the pressurized gas cartridge assembly that may be used in conjunction with an SIPFD according one or more embodiments.

In some embodiments, second tubing 50B is positioned inside the back of shirt 10 (see back view 18A in FIG. 1B) and may provide a connection between pressurized gas cartridge assembly 40 and torso inflation device 34A. Thus, pressurized gas cartridge assembly 40 may provide for automatic inflation of one or more bladders associated with each of the above-mentioned inflation devices. Note that gas cartridge assembly 40 may include one or more pressurized gas cartridges (not show in these figures but is shown in FIG. 3 element 42) to provide inflation of one or more bladders and provide flotation assistance to wearer 13.

Figure 1D:
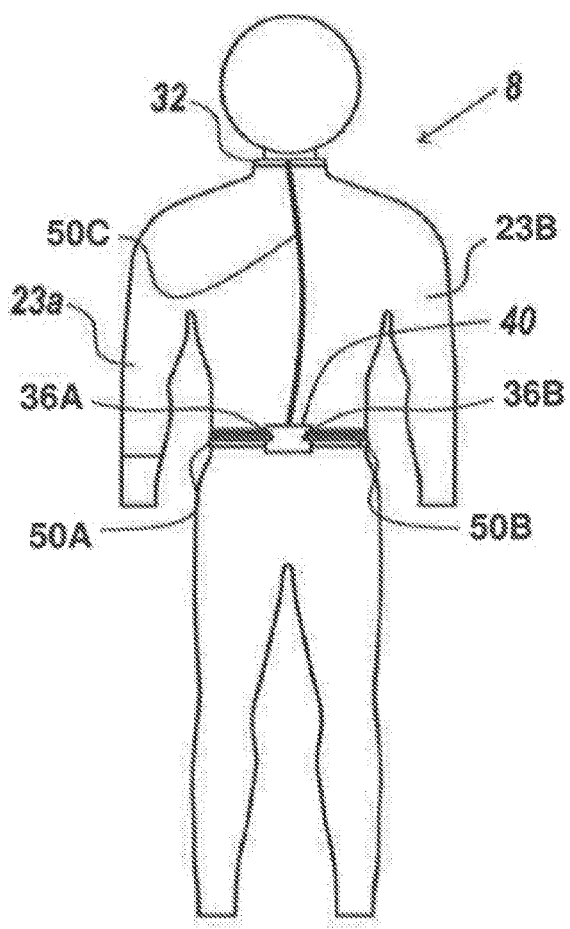

FIGS. 1C-1D depict a wetsuit 12 embodiment of the invention on a wearer 13A. Wetsuit 12 is illustrated in FIGS. 1C and 1D using a front view 16B and a back view 18B, respectively. As illustrated in each view, wetsuit 12 is to be secured to wearer 13A and provides at least two openings to which a sleeve may be attached, shown as sleeve 23A and 23B, respectively.

The SIPFD 8, in this example, is integrated with wetsuit 12 that is configured to be worn by a person or other living creature (e.g., wearer 13A). The SIPFD may communicate with a global communication network such as a satellite communication network, the Internet, or a similar network and a GPS network simultaneously.

As discussed above for shirt 10, wearable data transmitters 20A-B may similarly be positioned within, and secured to wetsuit 12, for example, at the wrist area 17A for data transmitter 20B and/or the torso area 11 for data transmitter 20A. Each wearable data transmitter 20A-B may be configured to communicate directly or indirectly (e.g., via additional networking components) with a global communication network and to the pressurized gas cartridge assembly 40 (e.g., via data busses or printed circuit boards ("PCBs")). In some cases, raw data may be transmitted while in other cases raw data may be analyzed prior to transmission of either the raw data itself or a result of analysis based on collected raw data. In any case, when pre-determined thresholds are crossed for different types of data (e.g., heartrate too high or heartrate too low) automatic transmission of data to the global communication network may take place in conjunction with automatic activation of flotation assistance. In some embodiments, automatic activation of flotation assistance may be provided prior to transmitting data to the global communication network. For example, a short delay in transmission may be desirable to allow for manual intervention to prevent "false alarms" or to allow time to surface prior to initiating transmission (e.g., conserve power that may otherwise be wasted by underwater transmissions that will not reach expected receivers).

Wetsuit 12 also includes neck inflation device 32 that may surround at least a portion of the neck of wearer 13A. Neck inflation device 32 may be configured to receive pressurized gas from the pressurized gas cartridge assembly 40 and may be secured to wetsuit 12. In some embodiments, neck inflation device 32 (for both shirt 10 and wetsuit 12) is designed to provide more relative flotation than other inflation devices or have bladders positioned in a manner such that, upon inflation, wearer 13A will be more likely to float in a "breathable position." As used herein, a breathable position indicates that upon activation of the assistance mechanisms of the SIPFD, the wearer 13A will be positioned with their face (i.e., including their nose and mouth) above the surface of the water (e.g., substantially on their back with their chest above water). In this manner, upon activation, wearer 13A will be caused to float on the surface of the water in a breathable position until further external assistance can be provided (e.g., until help responds—possibly in response to data transmission from the SIPFD on the global communication network). This orientation to a breathable position may be accomplished, in some embodiments, by design of bladder sizes relative to each other or by otherwise controlling an amount of gas provided to different bladders (e.g., via gas cartridge assembly 40).

In at least one of the disclosed embodiments, an overall torso inflation device of the SIPFD includes multiple torso inflation devices 34A, 34B and 34C as shown in FIGS. 1A-D. In some cases, (e.g., as seen in front views 16A-B), torso inflation device 34A is a lower U shape bladder extending from side to side of the shirt over the front of the torso. The overall torso inflation device of FIGS. 1A-C further include pair of upper oval-shaped bladder regions to make up torso inflation devices 34B and 34C. Each upper oval-shaped bladder of torso inflation devices 34B-C may be positioned over the pectoral muscles of the wearer 13A (or wearer 13 discussed above) between the skin and the shirt. The lower U shaped and upper oval-shaped bladders may be both configured to receive pressurized gas simultaneously (or at a predetermined time-offset from each other to facilitate a breathable position as discussed above). Each torso inflation device 34A-C may be secured in between the front of wetsuit 12 (or shirt 10) and the skin (e.g., closer to the skin side of the wearer based on the material used for shirt 10 or wetsuit 12). In some embodiments, each torso inflation device 34A-C may be embedded between layers of material used to form the wetsuit 12 (or shirt 10).

A set of mechanically activated emergency actuators 36A-B are, in some embodiments, mechanically connected with pressurized gas cartridge assembly 40 to: (i) inflate the neck and torso inflation devices; and (ii) deflate the neck and torso inflation devices by a wearer 13A or first responder.

In one embodiment, the back of wetsuit 11 (see back view 18B) includes the two openings 23A and 23B mentioned above to accommodate appendages of wearer 13A. Pressurized gas cartridge assembly 40 may be attached to the back of wetsuit 12 on the outside of wetsuit 12 such that gas cartridge assembly 40 is positioned away from the skin of wearer 13. Further gas cartridge assembly 40 may be positioned in the region of the body commonly referred to as the "small of the back" or in another region so as to not impede movement of wearer 13A. As seen in back view 18B, a first tube 50C inside the back of wetsuit 12 connects pressurized gas cartridge assembly 40 to neck inflation device 32. Further, a second tube 50B and a third tube 50C inside the back of the wetsuit 12 connects, in this example, pressurized gas cartridge assembly 40 to the torso inflation devices 34B and 34C.

Referring now to FIG. 2, a wearable data transmitter 20 as discussed above is illustrated in block diagram form to illustrate possible components of wearable data transmitter 20 and interaction with other components to provide one example embodiment of an SIPFD. Specifically, FIG. 2 illustrates wearable data transmitter 20 including functions that include communication through network communication device 14A for microprocessor 60A of wearable data transmitter 20. FIG. 2 further illustrates that microprocessor 60A may be in communication with each of data storage 65, a global network 14, and pressurized gas cartridge assembly 40 (e.g., either wired or wirelessly as illustrated).

In the example of FIG. 2, wearable data transmitter 20 encapsulates microprocessor 60A, data storage device 65, network communication device 14A, BLUETOOTH® device 46A, heartbeat device 22, water depth device 24, geo location device 26, and power supply 72A. As discussed above, heartbeat device 22 may be used for detecting heartbeat data (e.g., from wearer 13 or 13A) and forming an ECG and transmitting the detected heartbeat data to the microprocessor 60A. Water depth device 24 may be used for detecting the depth of the wearable data transmitter in a water column and transmitting the detected depth of the wearer to the microprocessor. Geolocation device 26 may be used for detecting longitude and latitude of the wearable data transmitter by using GPS and transmitting the data to the microprocessor.

In the example embodiment of FIG. 2, wearable data transmitter 20 is in communication with the pressurized gas cartridge assembly 40 via wireless BLUETOOTH® technology 46 to communicate to a microcontroller (not shown) of pressurized gas cartridge assembly 40. As illustrated in FIG. 2, pressurized gas cartridge assembly 40 includes a second BLUETOOTH® device 46B for communication with other components to implement disclosed functionality for an SIPFD.

In the example of FIG. 2, a power supply 72B is illustrated as providing power to the wearable data transmitter 20. Power supply 72B may include a battery sized to maintain sufficient power to maintain functionality of wearable data transmitter 20 for a pre-determined period of time. Battery or batteries that power wearable data transmitter 20 may be rechargeable and include a capability to be recharged utilizing solar power while in use.

In use, data may be received from heartbeat device 22, water depth device 24, and/or geolocation device 26 to be processed by microprocessor 60A. Processing may include communication with data storage 65 and a global communication network 14 (e.g., via network communication device 14A) to allow safety and health institutions 100 to access the wearers wearable data transmitter information in real time. Alternatively, wearable data transmitter 20 may be configured to communication with a nearby assistance ship such that at an event including a large number of concurrent swimmers (e.g., Triathlon) the assistance ship may monitor a number of SIPFDs simultaneously and be ready to provide immediate assistance for any competitor participating in the event.

Referring now to FIG. 3, pressurized gas cartridge assembly 40 is illustrated in more detail for one example implementation in accordance with disclosed embodiments. As illustrated in FIG. 3, pressurized gas cartridge assembly 40 fluidly connects neck inflation device 32 (from FIGS. 1A-D) and the torso inflation devices 34A-C (from FIGS. 1A-D) through tubing 50A, 50B and 50C (illustrated as only a portion of tubing in FIG. 3 that would, in practice, be connected to tubing having corresponding numbering and illustrated in FIGS. 1A-D). Further, a common supply tube 50D to supply gas from gas cartridge 42 and disperse that gas to each of tubes 50A-C concurrently is illustrated. In this example, both gas cartridge 42 and common supply tube 50D are illustrated as being connected to emergency hammer housing 44. In other embodiments, there may be multiple pressurized gas cartridge assembly 40 components for a single SIPFD or there may be more than one emergency hammer housing 44 to allow asynchronous supply of gas to different supply tubes.

In the example of FIG. 3, emergency hammer housing 44 further includes a BLUETOOTH® device 46B, which is in communication with wearable data transmitter 20 via BLUETOOTH® technology 46 (as shown in FIG. 2), for example. In some embodiments, wireless transmission may be used to initiate activation of spring and hammer 49 based on processing data received. For example, wireless data may be received and processed on built-in microprocessor 60B of gas cartridge assembly 40 that is in communication with microcontroller 48 connected to spring and hammer 49 to release the spring and hammer 49. Release of spring and hammer 49 is configured, in this example, to puncture an opening (not shown but actuated by puncture) associated with the pressurized gas cartridge 42. Upon puncture, gas escapes pressurized gas cartridge 42 to, in turn, inflate neck inflation device 32 and torso inflation devices 34A-C simultaneously (in this example through tubing 50A-D).

In one embodiment, emergency hammer housing 44 has two mechanically activated emergency actuators 36A and 36B built in. Each of the two mechanically activated emergency actuators 36A and 36B may, upon activation, mechanically enable spring and hammer 49 to puncture pressurized gas cartridge 42. As stated above, upon puncture, pressurized gas cartridge 42 may cause inflation of neck inflation device 32 and torso inflation devices 36A-C simultaneously. Finally, in one embodiment, emergency hammer housing 44 and its internal components are powered by a battery 72B. As stated above, battery 72B may be a rechargeable battery similarly configured as explained above for power supply 72A of FIG. 2.

Figure 4A:
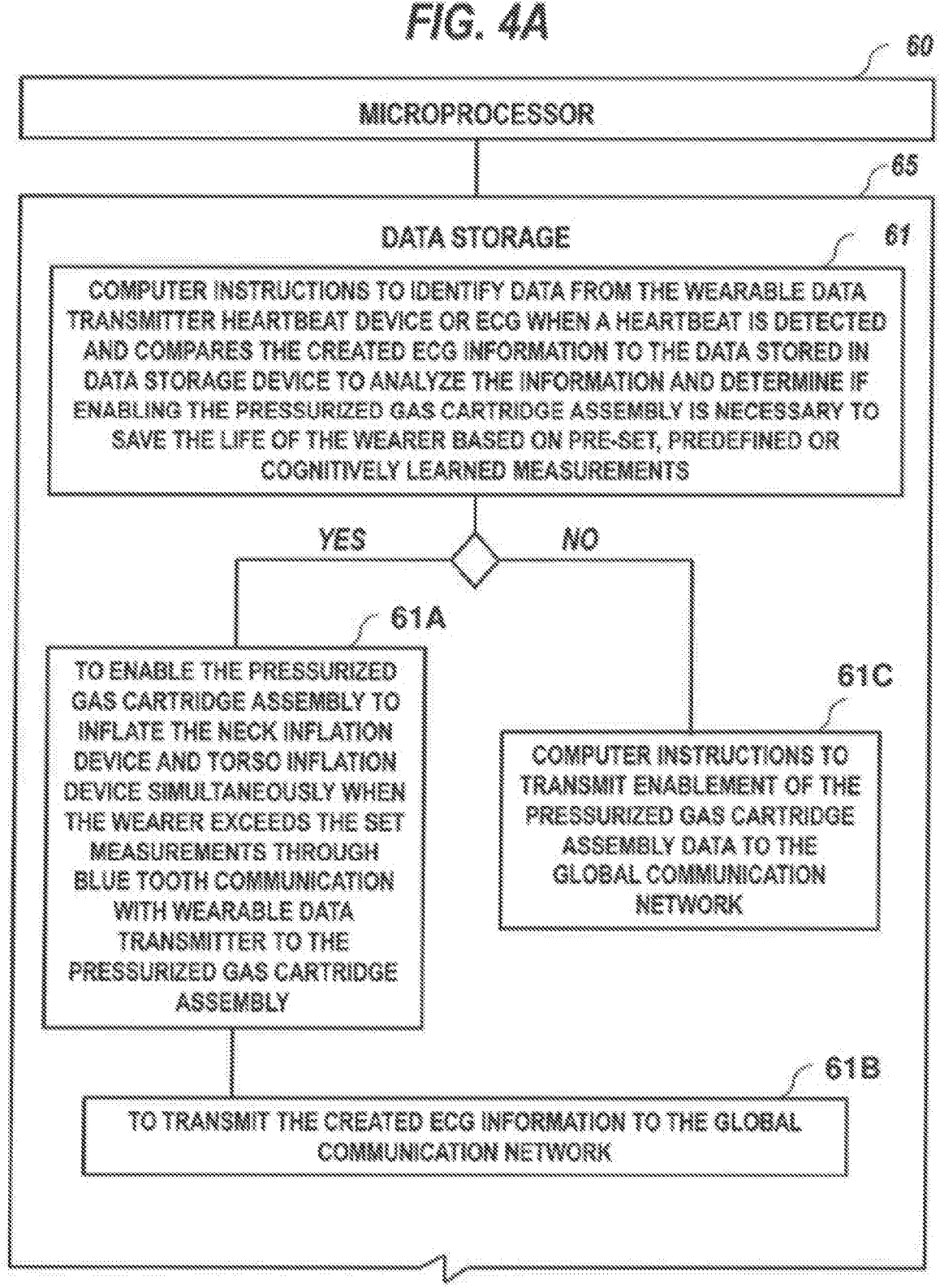

Referring now to FIGS. 4A-4C a data storage device 65 in communication with the microprocessor 60 (which may represent an example of microprocessor 60A of FIG. 2) is illustrated. In one example implementation, data storage device 65 includes computer instructions 61 to identify data from wearable data transmitter 20 heartbeat device 22 or an ECG generated from heartbeat monitoring. The instructions may detect and compare the created ECG information to additional data stored in data storage device 65. This detection and comparison may include processing to analyze the information and determine if enabling pressurized gas cartridge assembly 40 is necessary assist a wearer (e.g., wearer 13 or 13A discussed above). For example activation of flotation assistance may be initiated to save the life of the wearer based on pre-set, predefined or cognitively learned measurements. Computer instructions 61A may be used to enable pressurized gas cartridge assembly 40 to inflate the neck inflation device and torso inflation device in a number of ways depending on overall configuration of an SIPFD. For example, inflation may occur for all attached inflation devices when the wearer exceeds the set measurements through communication with wearable data transmitter 20, pressurized gas cartridge assembly 40, and a combination thereof. Further, computer instructions 61B may include instructions to transmit the created ECG information to the global communication network as updates and possibly to be used for later study. Finally, computer instructions 61C may be used to transmit information reflecting actions that cause enablement (e.g., puncture) of the pressurized gas cartridge assembly data to the global communication network for database updates and later study. In this manner, functionality of an SIPFD may be remotely recorded and utilized in a similar manner to a "black box" of an airplane for later study of criteria associated with an emergency event.

Data storage device 65 may further include computer instructions 64 to identify data from the wearable data transmitter 20 and water depth device 24 to compare the detected depth of wearable data transmitter 20 in a water column of a pre-set depth, width and length below the water's surface. This comparison may be used to analyze data stored in data storage device 65 and to analyze any additional information (e.g., current metrics) to determine if enabling pressurized gas cartridge assembly 40 is desired. For example, to aid, and possibly to save the life of an SIPFD wearer. Activation may be initiated, in part, based on pre-set and predefined measurements or learned information from stored data (e.g., using AI). Computer instructions 64A may be used to enable pressurized gas cartridge assembly 40 to cause inflation of the neck inflation device and torso inflation device as determined when the wearer of an SIPFD exceeds thresholds. Computer instructions 64B may be used to transmit the data from water depth device 24 to the global communication network 14 to be used as data base updates and for later study. Finally, computer instructions 64C may be used to transmit an indication of enablement (e.g., activation) of pressurized gas cartridge assembly 40 as activation data to the global communication network for data base updates and later study.

Data storage device 65 may include computer instructions 68 that may be used to identify data from wearable data transmitter 20, geolocation device 25, and combination of these and other components of an SIPFD implementation. Computer instructions 68 may be used to compare the longitude and latitude coordinates to the data stored in data storage device 65; to analyze the information; and determine if enabling the pressurized gas cartridge assembly is warranted. For example, to aid a wearer and possibly to save the life of the wearer. As mentioned above, activation may be based on pre-set and predefined coordinates and/or metrics. Computer instructions 68A may be used to enable the pressurized gas cartridge assembly to inflate the neck inflation device and torso inflation device. Inflation may be performed simultaneously or based on analysis of a wearer's current metrics. For example, activation at a shallow depth may differ from activation at a deeper depth. In any case, activation may occur when the wearer exceeds the set measurements as provided through communication between wearable data transmitter 20 and pressurized gas cartridge assembly 40. Computer instructions 68B may be used to initiate transmission of data from wearable data transmitter 20 and/or geolocation device 26 to global communication network 14 for data base updates and later study. Data base updates may initiate an alert for first responders if activation of pressurized gas cartridge assembly 40 in indicated. Computer instructions 68C may also be used to locally transmit instructions for enablement of pressurized gas cartridge assembly 40 and to provide data regarding enablement (e.g., activation) to global communication network 40 for data base updates, emergency response, later study, and any combination thereof.

In at least one embodiment, the power supply 72A that is part of wearable data transmitter 20 has a voltage from 3 to 12 DC volts. Similarly, in the same or a different embodiment, power supplied by battery 72B in pressurized gas cartridge assembly 40 is from 3 to 12 volts and is used to power the emergency hammer housing 44, BLUETOOTH® device 46B, microprocessor 60B, and microcontroller 48. Each power supply may be rechargeable. Each power supply may include at least one lithium-ion battery. Pressurized gas cartridge 40 may be refillable and replaceable. Multiple pressurized gas cartridges may be for a single gas cartridge assembly. Multiple gas cartridge assemblies may be used for a single SIPFD. In some cases, the each opening of the safety garment engages a detachable sleeve for covering an appendage of the wearer.

The following section provides a non-limiting example of use for an SIPFD according to disclosed embodiments.

An SIPFD is worn by athletes in a triathlon. The SIPFD is a shirt 10 or wetsuit 12 encapsulating a wearable data transmitter 20 and communicating with a global communication network 14 to provide information to first responders located at the triathlon or other safety and health institutes 100 accessing the information through to the global communication network 14.

Each SIPFD 8 is built into a shirt 10 or wetsuit 12 and configured to keep the wearers head above water via the pressurized gas cartridge assembly 40 in the event the wearer is having an emergency and unable to stay afloat in the water.

Wearable data transmitter 20 is secured to the torso 11 and/or wrist 17 area and configured to touch the athlete's skin and transmit heartbeat device 22 data, water depth device 24 data, and geolocation device 26 data. Data may be analyzed locally, or upon receipt via the global communication network, in order to detect, determine and initiate computer instructions of the SIPFD to enable pressurized gas cartridge assembly 40 to provide flotation assistance and possibly save the life of the wearer. Flotation assistance is provided by inflating the neck and torso inflation devices.

A neck inflation device 32 is comprised of a bladder built into the collar of the shirt 10 or wetsuit 12 to be physically about the neck of a wearer 13 or 13A. Neck inflation device 32 is configured to receive pressurized gas in the event of an emergency and keep the wearers head above water.

A torso inflation devices 34A-C are configured to the front torso area whether the abdominal, pectoral areas or both of the wearer of the shirt 10 or wetsuit 12. Torso inflation devices 34A-C, configured to receive pressurized gas in the event of an emergency, may be assist in keeping the wearer afloat and the torso area above water to prevent the wearer from flipping on one's back.

A pressurized gas cartridge assembly 40 is attached to the back of the shirt 10 or wetsuit 12. Pressurized gas cartridge 42 is connected to the emergency hammer housing 44 which fluidly connects the neck inflation device 32 and the torso inflation device 34A, 34B, 34C through supply tubing 54 that is connected to each of tubing 50A, 50B, 50C. The pressurized gas cartridge contains carbon dioxide and operates at a pressure of 75 psi.

The pressurized gas cartridge assembly 40 is electronically enabled (punctured) through the emergency hammer housing 44 to release the pressurized gas into the connected tubing 50D and thus each of tubing 50A, 50B, and 50C to inflate the neck inflation device 32 and torso inflation devices 34A-C.

A mechanically activated emergency actuator 36B mechanically enables the pressurized gas cartridge assembly 40 to: (i) inflate the neck and torso inflation devices; and (ii) deflate the neck and torso inflation devices by a wearer.

While these embodiments have been described with emphasis on the embodiments, it should be understood that within the scope of the appended claims, the embodiments might be practiced other than as specifically described herein.

What is claimed is:

1. A self-inflating personal flotation device ("SIPFD") comprising:
    a safety garment comprising:
        a front for at least partially covering a chest of a wearer; and
        a back for at least partially covering a back of the wearer, the back secured to the front and providing an opening for one or more appendages of the wearer;
    a wearable data transmitter connected to the safety garment and configured to touch the wearer, the wearable data transmitter configured to detect a heart rate, water depth, and geolocation of the wearer;
    a neck inflation device secured to the safety garment and configured to receive a pressurized gas;
    a torso inflation device secured to the safety garment and configured to receive the pressurized gas; and
    a pressurized gas cartridge assembly comprising:
        a pressurized gas cartridge fluidly connected to the neck inflation device and to the torso inflation device to provide the pressurized gas to the neck inflation device and the torso inflation device;
        a microprocessor communicating with the wearable data transmitter to trigger automatic inflation of both the neck inflation device and the torso inflation device based on information received from the wearable data transmitter; and
        an emergency actuator triggered by the microprocessor to manually and mechanically enable the pressurized gas cartridge to: (i) inflate the neck inflation device and the torso inflation device; and (ii) deflate the neck inflation device and the torso inflation device.

2. The SIPFD of claim 1, wherein the gas cartridge assembly is communicatively coupled to the wearable data transmitter using a wired connection or a wireless connection.

3. The SIPFD of claim 2, wherein the microprocessor of the gas cartridge assembly communicating with the wearable data transmitter executes computer instructions to identify a heart rate of the wearer from the wearable data transmitter and compare Electrocardiogram ("ECG") information to determine if triggering the pressurized gas cartridge assembly is indicated based on pre-set, predefined, or cognitively learned measurements.

4. The SIPFD of claim 2, wherein the microprocessor of the gas cartridge assembly communicating with the wearable data transmitter includes computer instructions to identify the water depth of the wearer from the wearable device and compare the water depth to determine if triggering the pressurized gas cartridge assembly is indicated based on pre-set, predefined measurements.

5. The SIPFD of claim 2, wherein the microprocessor of the gas cartridge assembly communicating with the wearable data transmitter includes computer instructions to identify a geolocation of the wearer from the wearable device and compare the geolocation to determine if triggering the pressurized gas cartridge assembly is indicated based on pre-set, predefined measurements.

6. The SIPFD of claim 1, wherein the pressurized gas cartridge is rechargeable and replaceable.

7. The SIPFD of claim 1, wherein the wearable data transmitter is located on a front torso area, sleeves attached to the front and the back, within the gas cartridge assembly, or at a wrist area of the wearer.

8. The SIPFD of claim 1, wherein the opening for one or more appendages connects a detachable sleeve for covering an appendage of the wearer.

9. The SIPFD of claim 1, further comprising tubing inside the back to fluidly connect the pressurized gas cartridge assembly to the neck inflation device.

10. The SIPFD of claim 1, further comprising at least one tubing section inside the back to fluidly connect the pressurized gas cartridge assembly to the torso inflation device.

11. The SIPFD of claim 1, further comprising:
   at least one power supply to power the wearable data transmitter and one or more components in the pressurized gas cartridge assembly.

12. The SIPFD of claim 11, wherein the at least one power supply includes independent power sources for the wearable data transmitter and the one or more components.

13. The SIPFD of claim 1, wherein the wearable data transmitter communicatively connected to the microprocessor of the gas cartridge assembly is further configured to communicate with a global or local network.

14. The SIPFD of claim 13, wherein the wearable data transmitter is further configured to execute computer instructions to transmit a location of the wearer to the global or local network, the transmitted location associated with a triggering event of the gas cartridge assembly for notification of first responders or event assistance.

15. The SIPFD of claim 13, further comprising:
   a geolocation device detecting longitude and latitude of the wearer using a global positioning system,
   wherein the microprocessor is further configured to execute computer instructions to transmit location data determined by the geolocation device to the global or local network.

* * * * *